(12) United States Patent
Taylor

(10) Patent No.: US 9,907,653 B2
(45) Date of Patent: Mar. 6, 2018

(54) PUMP BULB FOR AN IMPLANTABLE PENILE PROSTHETIC

(71) Applicant: Coloplast A/S, Humlebaek (DK)

(72) Inventor: Jeffrey Brian Taylor, Forest Lake, MN (US)

(73) Assignee: Coloplast A/S, Humlebaek (DK)

( * ) Notice: Subject to any disclaimer, the term of this patent is extended or adjusted under 35 U.S.C. 154(b) by 273 days.

(21) Appl. No.: 14/809,286

(22) Filed: Jul. 27, 2015

(65) Prior Publication Data

US 2017/0027696 A1    Feb. 2, 2017

(51) Int. Cl.
*A61F 5/00*    (2006.01)
*A61F 2/26*    (2006.01)

(52) U.S. Cl.
CPC ..................... *A61F 2/26* (2013.01)

(58) Field of Classification Search
CPC ......................................... A61F 2/26
USPC ..................................... 600/38–41
See application file for complete search history.

(56) References Cited

U.S. PATENT DOCUMENTS 5,163,897 A    11/1992  Persky
6,991,601 B2    1/2006  Kuyava et al.

FOREIGN PATENT DOCUMENTS

| EP | 2839809 A1 | 2/2015 |
| WO | 9321872 A1 | 11/1993 |
| WO | 2014201382 A1 | 12/2014 |

OTHER PUBLICATIONS

1st Office Action dated Dec. 4, 2015 from DK Patent Office.
2nd Office Action dated Mar. 2, 2016 from DK Patent Office.

*Primary Examiner* — John Lacyk
(74) *Attorney, Agent, or Firm* — Coloplast Corp., Coloplast A/S; Nick Baumann

(57) ABSTRACT

A penile prosthetic includes an inflatable member that is implantable into a penis of a user, a reservoir that is implantable in an abdomen, and a pump. The pump is configured to be attached between the inflatable member and the reservoir and is implantable in a scrotum. The pump includes a pump bulb formed by first and second end sections, a mid-section and concave portions.

19 Claims, 13 Drawing Sheets

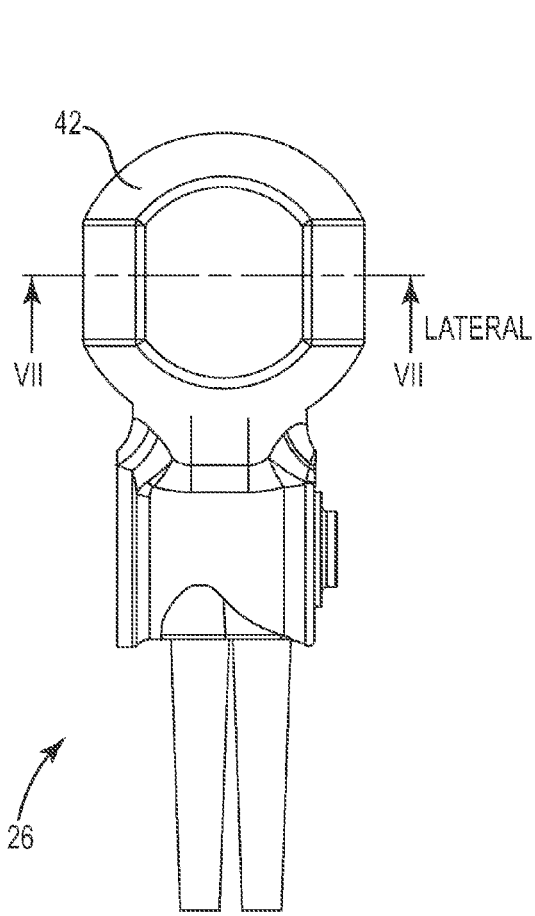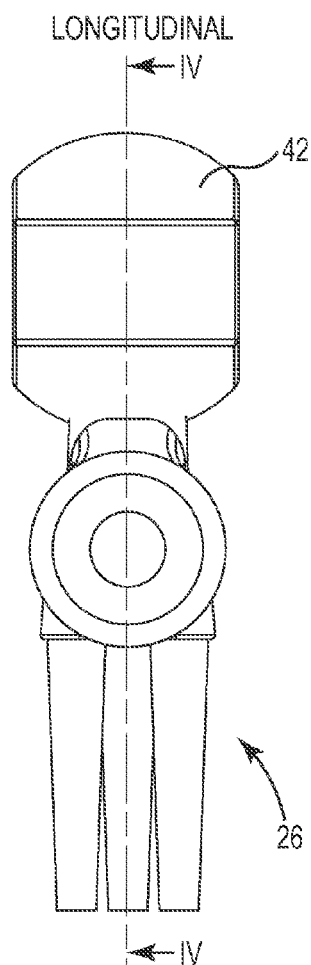
Fig. 3B
Fig. 3A
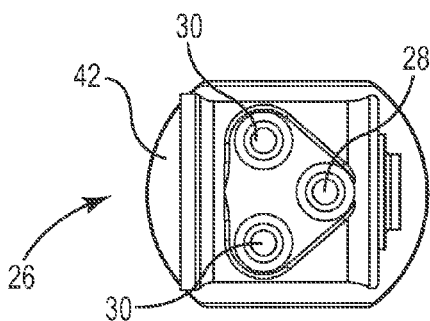
Fig. 3C

US 9,907,653 B2

PUMP BULB FOR AN IMPLANTABLE PENILE PROSTHETIC

BACKGROUND

An implanted penile prosthetic is effective in relieving erectile dysfunction in men.

A penile prosthetic typically includes an inflatable cylinder that is implanted in each corpora cavernosum of the penis, a reservoir implanted in the abdomen that communicates with the cylinders, and a pump, often located in the scrotum, that is employed to move liquid from the reservoir into the cylinders for inflation of the implanted cylinders.

In a typical application, the user squeezes a bulb of the pump multiple times to draw liquid out of the reservoir and pump the liquid into the cylinders. The repeated squeezing of the bulb thus moves the liquid from the reservoir into the cylinders to provide the user with an erect penis. The user may return the penis to its flaccid state by selectively transferring the liquid from the cylinders back into the reservoir.

Some users suffer from a reduced range of motion in their fingers or from reduced dexterity, at times due to arthritis of the hand. These users can have difficulty in grasping the pump bulb or in repeatedly squeezing the pump bulb.

Penile prostheses have proven effective in relieving erectile dysfunction in men. However, users and their surgeons would welcome improvements to penile prostheses.

SUMMARY

Aspects of the disclosure provide an implantable penile prosthetic including a pump according to the appended claims.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated, as they become better understood by reference to the following detailed description. The elements of the drawings are not necessarily to scale relative to each other. Like reference numerals designate corresponding similar parts.

FIG. 3A is a top view of one embodiment of the pump illustrated in FIG. 1 and indicating the location of a longitudinal cross-sectional view of FIG. 4.

FIG. 3B is a side view of one embodiment of the pump illustrated in FIG. 1 and indicating the location of a lateral cross-sectional view of FIG. 7.

FIG. 3C is an end side view of one embodiment of the pump illustrated in FIG. 1.

DETAILED DESCRIPTION

Figure 1:
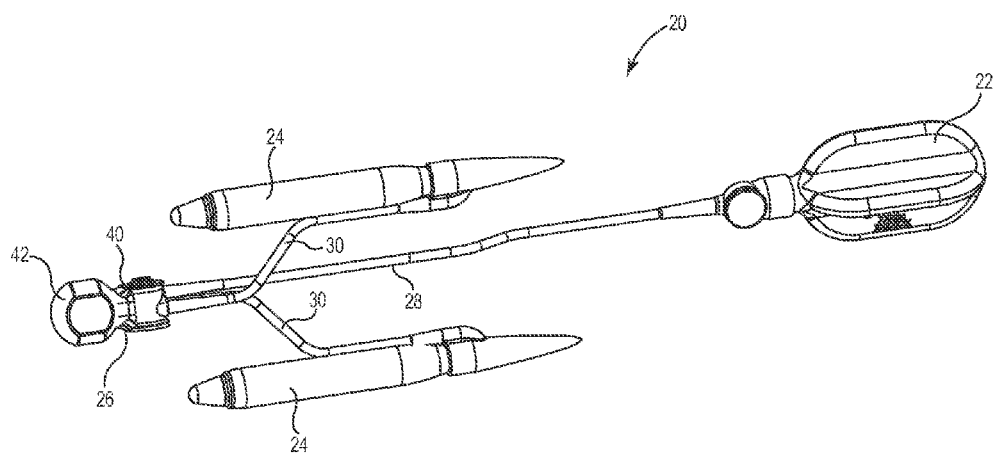
FIG. 1 is a perspective view of one embodiment of an implantable penile prosthetic including a pump attached to inflatable penile inserts and a reservoir.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The term "proximal" as employed in this application means that the referenced part is situated next to or near the point of attachment or origin or a central point: as located toward a center of the human body. The term "distal" as employed in this application means that the referenced part is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal, and of the crus of the penis is located proximal relative to the male body such that a distal end of a corpora cavernosum of the patient extends about midway into the glans penis.

Embodiments provide an implantable penile prosthetic including a pump that is provided with a pump bulb that is easier to grasp and easier to pump, particularly for those users who suffer from arthritis or limited dexterity of the hand. Embodiments provide a pump having a pump bulb including first and second end sections, each formed as a portion of a sphere, a planar mid-section extending between the first end section and the second end section and a concave portion extending between a first apex located in the first end section and a second apex located in the second end section. The concave portion provides a finger access area to configure the pump bulb to more naturally fit in the hand between the fingers of the user.

Embodiments provide a pump having a pump bulb with an internal cavity defined by an external surface, the external surface having six interconnected segments including a side segment forming a concavity.

In contrast, some implantable penile prosthetics are provided with a completely spherical pump bulb that operates to pump liquid from the prosthetic reservoir to the penile implants. However, some users have experienced sliding and movement of the completely spherical pump bulb within the tissue of the scrotum that presents challenges in grasping and/or repeatedly pumping the completely spherical pump bulb. The pump bulb described below includes a concave portion extending between a first apex located in the first end section and a second apex located in the second end section providing an improved finger-grasping surface with an easier to manipulate pump, particularly for users with limited dexterity.

FIG. 1 is a perspective view of one embodiment of an implantable penile prosthetic 20. The penile prosthetic 20 includes a reservoir 22 communicating with inflatable members 24 across a pump 26. The reservoir 22 is connected with the pump 26 by tubing 28, and inflatable members 24 are connected with the pump 26 by tubing 30.

The components (reservoir 22, implants 24, pump 26, and tubing 28, 30) of the penile prosthetic 20 are generally provided unassembled in a kit of parts. The components are assembled immediately prior to surgery, or intra-operatively, as determined by the surgeon. For example, each of the tubing lengths 28, 30 have a portion that is attached to the reservoir 22 and a portion that is attached to the inflatable members 24, respectively, and a portion that is secured to a pump housing 40 that extends from a pump bulb 42 of the pump 26. The tubing lengths are attached by some form of tubing connector useful with surgical implants. The components of the penile prosthetic 20 are illustrated in an assembled configuration in FIG. 1 for descriptive clarity.

The reservoir 22 is sized for implantation within the human body, for example within the abdomen. The reservoir 22 is configured to retain a volume of liquid useful in inflating the inflatable members, for example with a volume in a range of 50-350 cc. Suitable materials for fabricating the reservoir 22 include silicone, polymers such as urethanes, a blend of polymers with urethane, copolymers of urethane, or the like. In one exemplary fabrication process, one of the suitable materials identified above is moulded into a container shape appropriate for implantation in the space of Retzius or in the abdomen.

The inflatable members 24 are provided as a pair of inflatable cylinders, each of which is sized to be implanted into a corpora cavernosum of the penis. Each of the cylinders includes a rear tip that is implanted toward the crus of the penis and a distal end that is implanted within the glans penis. The cylinders are fabricated from material configured to collapse and be flexible when the cylinders are deflated to provide the penis with a flaccid state and expand when the cylinders are inflated with liquid to provide the penis with an erect state. Suitable material for fabricating the cylinders 32 includes silicone, polymers such as urethanes, a blend of polymers with urethane, copolymers of urethane, or the like. Suitable cylinders are available from Coloplast Corp., Minneapolis, Minn.

Figure 2:
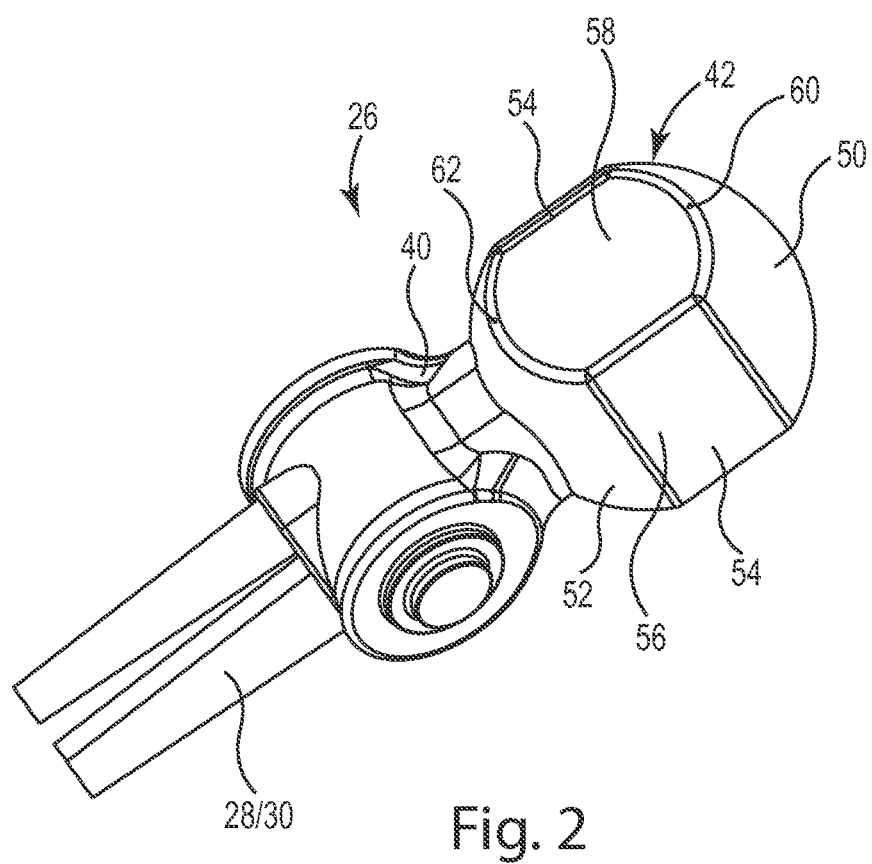
FIG. 2 is a perspective view of one embodiment of the pump illustrated in FIG. 1.

FIG. 2 is a perspective view of the pump 26 according to one embodiment.

In one embodiment, the pump housing 40 is attached to the pump bulb 42 and includes valve assemblies (described below) in communication with conduits that extend from the pump housing 40 for attachment with the tubing 28, 30. The valve assemblies facilitate controlling of the fluid to inflate and deflate the cylinders 32, respectively.

Figure 4:
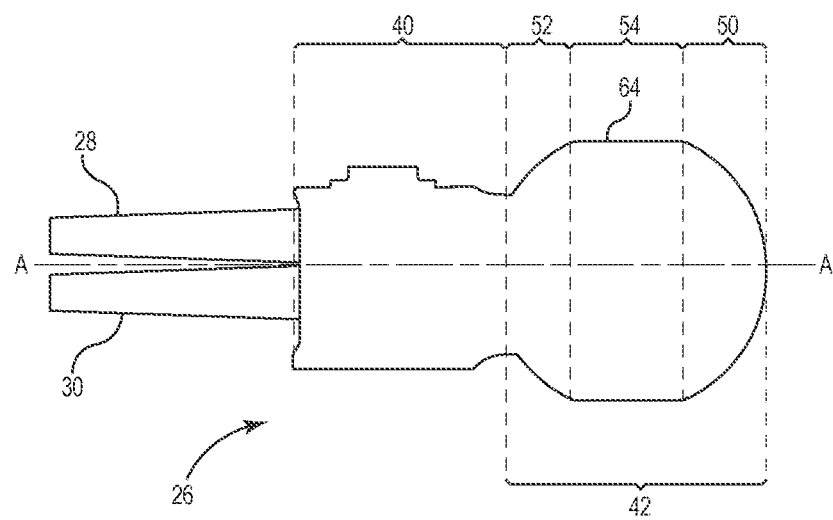
FIG. 4 is a schematic, longitudinal cross-sectional view taken along the line IV-IV in FIG. 3A.
Figure 7:
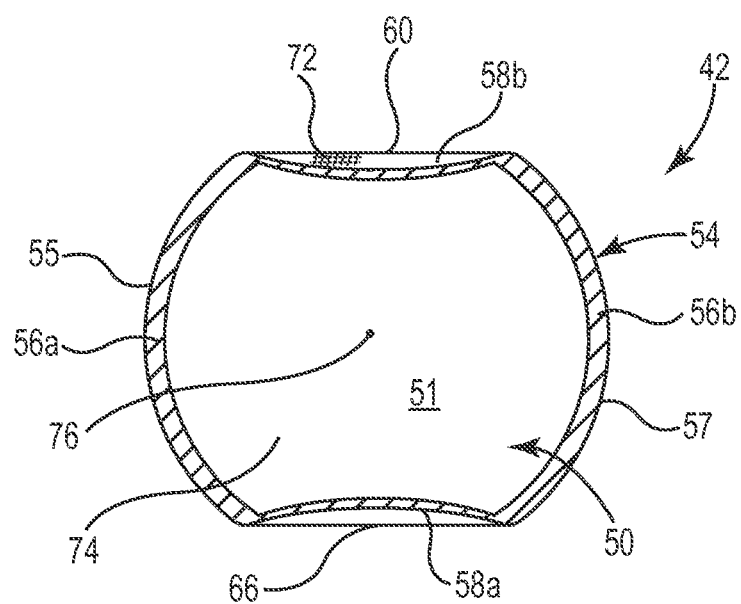
FIG. 7 is a lateral cross-sectional view of one embodiment of the pump bulb taken along the line VII-VII in FIG. 3B.

The pump bulb 42 includes a first end section 50 and a second end section 52. Each one of the first end section 50 and the second end section 52 is formed as a portion of a sphere. It is to be understood by the wording "portion of a sphere" that each of the first end section 50 and the second end section 52 is configured to provide a surface of the pump bulb 42 formed as a portion of the surface of a sphere. The pump bulb 42 includes a mid-section 54 that is extending between the first end section 50 and the second end section 52. The mid-section 54 is planar when seen in longitudinal cross-section through the pump bulb 42 (FIGS. 3A, 4). The mid-section 54 forms an arc 56 when seen in lateral cross-section through the pump bulb 42 (FIGS. 3B, 7). In one embodiment, the arc 56 is a circular arc. The pump bulb 42 includes a concave portion 58 extending between a first apex 60 located in the first end section 50 and a second apex 62 located in the second end section 52. In one embodiment, the second end section 52 is attached to the pump housing 40. In one embodiment, the pump bulb 42 is monolithically formed with the pump housing 40 at the second end section 52.

FIG. 3A is a schematic top view of the pump 26 indicating the position of the longitudinal cross-section through the pump bulb 42 of FIG. 4.

FIG. 3B is a schematic side view of the pump 26 indicating the position of the lateral cross-section through the pump bulb 42 of FIG. 7.

FIG. 3C is an end view of the pump 26 seen from an end opposite the location of the pump bulb 42 and indicating the tubing 28, 30.

FIG. 4 is a schematic, longitudinal cross-sectional view taken along the line IV-IV in FIG. 3A illustrating an overall contour of the pump and pump bulb.

In FIG. 4, the mid-section 54 has a planar extent extending between the first end section 50 and the second end section 52. The planar mid-section 54 is connected between the spherical portions for the first and second end sections 50, 52. It is to be understood that the planar extent of mid-section 54 means that an external surface 64 of the mid-section 54 extends parallel with a longitudinal axis A-A through the pump 26. The mid-section 54 is planar when seen in longitudinal cross-section through the pump bulb 42. In other words, the external surface 64 of the pump bulb 42 along the mid-section 54 is parallel to the axis A-A when seen in longitudinal cross-section through the pump bulb 42. The external surface 64 of the mid-section 54 is planar and takes the shape of a straight line between the first and second end sections 50, 52 when seen in longitudinal cross-section through the pump bulb 42. The second end section 52 of the pump bulb 42 is attached to the pump housing 40. The tubing 28, 30 extends from the pump housing 40.

Figure 5:
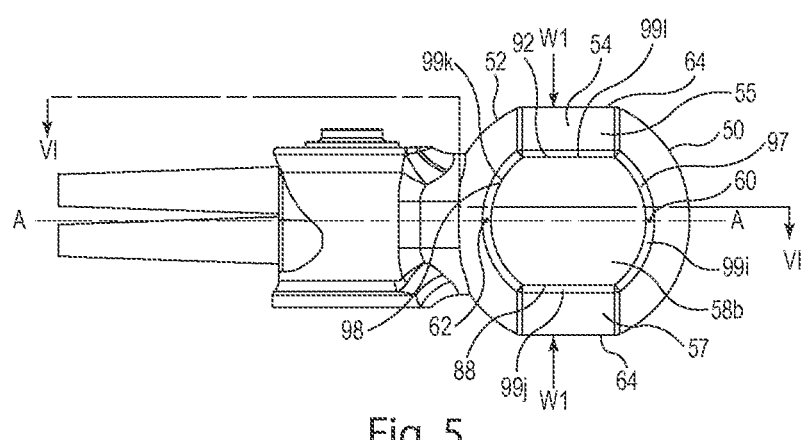
FIG. 5 is a side view of one embodiment of the pump including a pump bulb.
Figure 6:
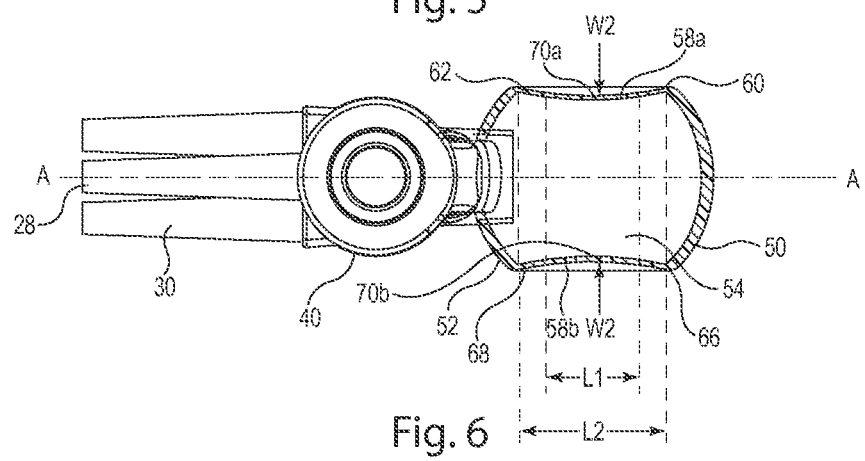
FIG. 6 is a partially sectional top view of the bulb of the pump taken along the line V-V indicated in FIG. 5.

FIG. 5 is a schematic side view of the pump 26 also indicating the position of the partially sectional top view of FIG. 6 taken along line VI-VI.

In FIG. 6, a portion of the pump 26 including the housing 40 and the tubing 28, 30 is viewed in a regular top view and a portion including the pump bulb 26 in shown at a section line through the pump bulb 26 to illustrate sections of the pump bulb 26.

FIGS. 5 and 6 show the first and second end sections 50, 52 and the mid-section 54. As in FIG. 4, the side view of FIG. 5 also shows the mid-section 54 with the planar external surface 64 extending between the first end section 50 and the second end section 52. FIG. 6 shows a first concave portion 58a extending between the first apex 60 located in the first end section 50 and the second apex 62 located in the second end section 52. In one embodiment (as illustrated in FIG. 6), the pump bulb 42 includes a second concave portion 58b extending between a third apex 66 located in the first end section 50 and a fourth apex 68 located in the second end section 52. The second concave portion 58b is separate from the first concave portion 58a. In one embodiment, the first concave portion 58a and the second concave portion 58b are located on opposite sides of the pump bulb 26, with the mid-section 54 connected between the first concave portion 58a and the second concave portion 58n. In one embodiment, the first concave portion 58a and the second concave portion 58b face in opposite directions of each other in relation to the longitudinal A-A through the pump 26. This configuration of the concave portions 58a, 58b helps provide easier tactile recognition of the concave portions 58a, 58b of the pump bulb 42 through a skin surface when the user is looking to locate the gripping surfaces for engagement of the pump to create an erection of the penis.

In one embodiment, a first width W1 of the pump bulb 42 between an external surface of the concave portion 58a and an external surface of the concave portion 58b is greater than a second width W2 of the pump bulb 42 between planar extent surfaces 64 of the mid-section 54. In one embodiment, the pump bulb is configured such that width W2 is smallest between a vertex 70a of the concave portion 58a and a vertex 70b of the concave portion 58b.

In embodiments, a first longitudinal extent L1 of the mid-section 54 is shorter than a second longitudinal extent L2 of a concave portion 58a, 58b between the first apex 60 and the second apex 62, and/or between the third apex 66 and the fourth apex 68, respectively. In other words, in embodiments the longitudinal extent of the mid-section 54 is different from a longitudinal extent of the concave portion 58 measured between respective apices.

FIG. 7 is a lateral cross-sectional view of one embodiment of the pump bulb 42 taken along the line VII-VII in FIG. 3B. The cross-sectional view is located at the mid-section 54 of the pump bulb 42. In one embodiment, a boundary of the mid-section 54 is formed by a plurality of discrete segments 55, 57. In embodiments, each segment 55, 57 of a plurality of discrete segments forms an arc 56 in lateral cross-section. In embodiments, the plurality of discrete segments combine to configure the mid-section 54 to form an arc in lateral cross-section. In one embodiment, the mid-section 54 includes two discrete segments 55, 57 each forming a circular arc 56a, 56b. In the cross-section of FIG. 6, the circular arc 56a has a curved extent between the first concave portion 58a and the second concave portion 58b. The circular arc 56a, 56b defines a curve in the plane of the paper. In one embodiment, the mid-section 54 includes a first arc-shaped segment 55 and a second arc-shaped segment 57, each of the first and the second arc-shaped segment 55, 57 extending between the first concave portion 58a and the second concave portion 58b. FIG. 7 also shows an internal surface 51 of the first end section 50 (to be understood as bulging away from the observer and away from the plane of the paper). Also visible is the first apex 60 and the third apex 66. In embodiments, the concave portions 58a, 58b are adapted to form a finger gripping (or grasping) area of the pump bulb 42. In one embodiment, the concave portions 58a, 58b include a friction-increasing surface 72, such as, but not limited to a criss-cross surface pattern. FIG. 7 also indicates an internal cavity 74 of the pump bulb 42. The internal cavity 74 is defined (surrounded) by the first and second end sections 50, 52, the first and second arc-shaped segments 55, 57 and the first and second concave portions 58a, 58b.

In one embodiment, the pump bulb 26 includes a second concave portion 58b separate from the first concave portion 58a, wherein the mid-section 54 includes a band that is connected between the first concave portion 58a and the second concave portion 58b, and the band is narrower than a width of either of the first concave portion 58a and the second concave portion 58b.

In embodiments, the concave portion 58 is bounded by a first curved line located in the first end section 50 and a second curved line located in the second end section 52, where the concave portion 58 and the first and second curved lines form a finger gripping area of the pump bulb 26.

In one embodiment, the concave portion 58 has a boundary provided by a first curved line located in the first end section 50, a second curved line located in the second end section 52, and a pair of separated and parallel linear lines connected between the first curved line located in the first end section 50 and the second curved line located in the second end section 52.

The concave portions 58a, 58b are each sized to receive a thumb or a finger of the user. The distinct difference of the surface configurations of the concave portion 58a, 58b and the sphere shape of the first and second end sections 50, 52 provides a pump bulb 42 wherein the grasping surfaces provided by the concave portions 58a, 58b are easily located by the user when he palpates the skin surface of the scrotum. Contrary to the case of some prostheses incorporating completely spherical pump bulbs, each of the concave portions 58a, 58b of the pump bulb 42 provides a rest for the user's thumb or other finger, which helps stabilize the pump 26 and further helps prevent the pump bulb 42 from unintentionally slipping out between the fingers of the user. Each of the first and second end sections 50, 52 is sized and configured to provide a wide obstacle that helps resist slipping through the user's fingers when the user squeezes the concave portions 58a, 58b of the pump bulb 42. In this manner, the pump bulb 42 has increased stability during compression compared to a completely spherical bulb and is therefore easier to use and squeeze for those who suffer from arthritis and limited dexterity.

Moreover, the increased stability of the pump bulb 42 helps facilitate use of less force for squeezing and engaging the pump bulb 42 and this additionally means that the user's overall tactile perception of the pumping procedure is improved. Improved stability and a reduction of the required squeezing force of the pump bulb 42 is particularly, but not exclusively, useful when the user is familiarizing himself with the penile prosthesis in the period following healing and initially learning to apply pressure to the pump bulb 42. Even further, squeezing of oppositely facing concave portions 58a, 58b delivers an increased and more effective evacuation force as compared to completely spherical pump bulbs, and this makes squeezing of the pump bulb 42 more efficient in delivering liquid to the cylinders 24.

In embodiments, the disclosure relates to an implantable penile prosthetic having a pump 26 including a pump bulb 42 having an internal cavity formed by an external surface including six interconnected segments. It is to be understood that the term "interconnected" is not intended to imply that each individual segment is necessarily connected to each and all of the other five segments. Instead, the six segments combine to define an internal cavity of the pump bulb such that the pump bulb is capable of holding liquid in the internal cavity during a pumping action.

With reference to FIGS. 4-7, in one embodiment the pump bulb 42 includes a top segment 50 formed as a portion of a top sphere surface, with a centre of the top sphere surface offset away from a centre 76 of the internal cavity 74. The pump bulb 42 includes a bottom segment 52 formed as a portion of a bottom sphere surface, with a centre of the bottom sphere surface offset away from the centre 76 of the internal cavity 74. The pump bulb 42 includes a first arc-shaped side segment 55 and a second arc-shaped side segment 57, each of the side segments 55, 57 connecting the top segment 50 with the bottom segment 52. The pump bulb 42 includes a third side segment 58a shaped as a portion of a sphere and a fourth side segment 58b shaped as a portion of a sphere. Each of the third and fourth side segments 58a, 58b connects the top segment 50 with the bottom segment 52 such that the external surface at the third side segment 58a and the fourth side segment 58b defines a concavity.

Figure 8:
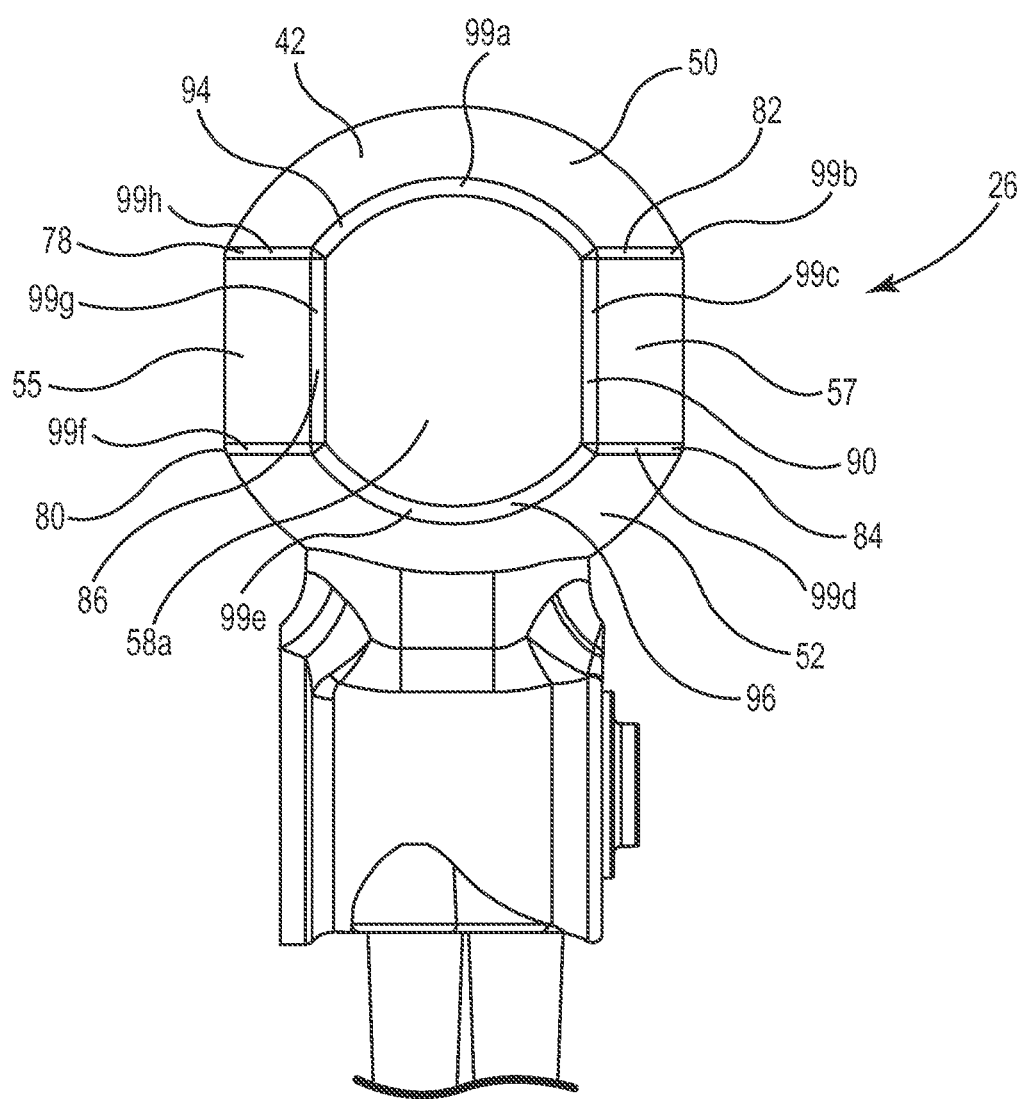
FIG. 8 is a side view of one embodiment of the pump seen from a side facing opposite the side visible in FIG. 5.

FIG. 8 is a side view of one embodiment of a pump 26 including a pump bulb 42. In one embodiment, the first arc-shaped side segment 55 is connected to the top segment 50 along a first curved line 78 and to the bottom segment 52 along a second curved line 80. The second arc-shaped side segment 57 is connected to the top segment 50 along a third curved line 82 and to the bottom segment 52 along a fourth curved line 84.

In one embodiment, the first arc-shaped side segment 55 is connected to the third side segment 58a along a first straight line 86 and to the fourth side segment 58b along a second straight line 88 (see FIG. 5). The second arc-shaped side segment 57 is connected to the third side segment 58a along a third straight line 90 and to the fourth side segment 58b along a fourth straight line 92 (see FIG. 5).

In one embodiment, the third side segment 58a is connected to the top segment 50 along a fifth curved line 94 and to the bottom segment 52 along a sixth curved line 96. The fourth side segment 58b is connected to the top segment 50 along a seventh curved line 97 and to the bottom segment 52 along an eighth curved line 98 (see FIG. 5).

In embodiments, the pump bulb 42 includes a transition area 99a-99h (FIG. 8), 99i-99l (FIG. 5) between any two adjacent segments 50, 52, 55, 57, 58a, 58b. In embodiments, this is advantageous in that it helps provide clearly defined and differentiated segments, in turn aiding in tactile recognition of the relevant gripping surfaces of the pump bulb 42 through the skin surface after implantation of the prosthesis. Moreover, the transition area 99a-99i helps provide a smooth, edge- or ridge-free surface of the pump bulb 42 for implantation.

In one embodiment, the transition area 99a-99l is defined by a plane surface, i.e. the transition area extends along a straight line between two neighbouring segments. In one embodiment, the transition area 99a-99l is defined by a curved surface, i.e. the transition area extends along an arc between two neighbouring segments.

Figure 9A:
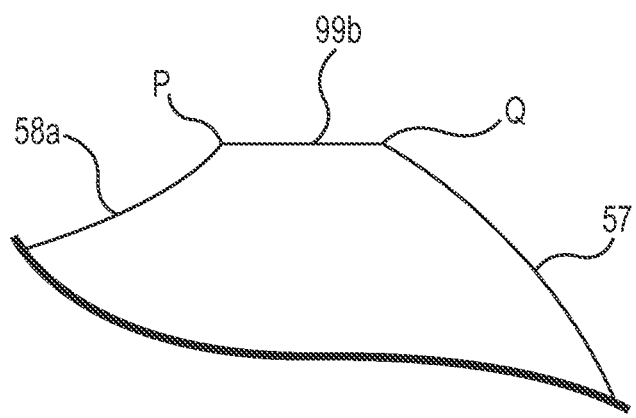
FIG. 9A is an enlarged, schematic cross-sectional view of one embodiment of a transition area of the pump bulb.

FIG. 9A is an enlarged, schematic view of one exemplary transition area, in this example transition area 99b between second side segment 57 and third side segment 58a. In FIG. 9A the transition area 99b is defined by a plane surface, i.e. the transition area extends along a straight line between intersection point P at third side segment 58a and intersection point Q and the second side segment 57.

Figure 9B:
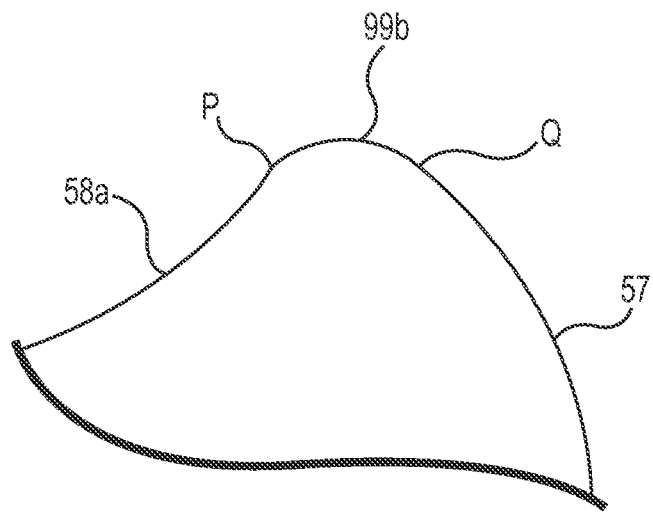
FIG. 9B is an enlarged, schematic cross-sectional view of one embodiment of a transition area of the pump bulb.

FIG. 9B is a schematic view of exemplary transition area 99b in one embodiment wherein the transition area is defined by a curved surface, i.e. the transition area extends along an arc between intersection point P at third side segment 58a and intersection point Q and the second side segment 57.

In embodiments, the pump bulb 42 includes intersection points between three neighbouring segments wherein the transition area can curve in more than one dimension, or can include a polygonal surface area defined by more than one straight line. Such intersection point configurations are advantageous in that they provide a smooth transition between multiple segments having differentiated external surfaces.

In one embodiment, the disclosure provides a pump bulb 42 having a finger pad 58a, 58b extending between four segments 50, 52, 55, 57. In one embodiment, the disclosure provides a pump bulb 42 including a finger gripping area in a concavity 58a, 58b defined by four segments 50, 52, 55, 57.

Figure 10:
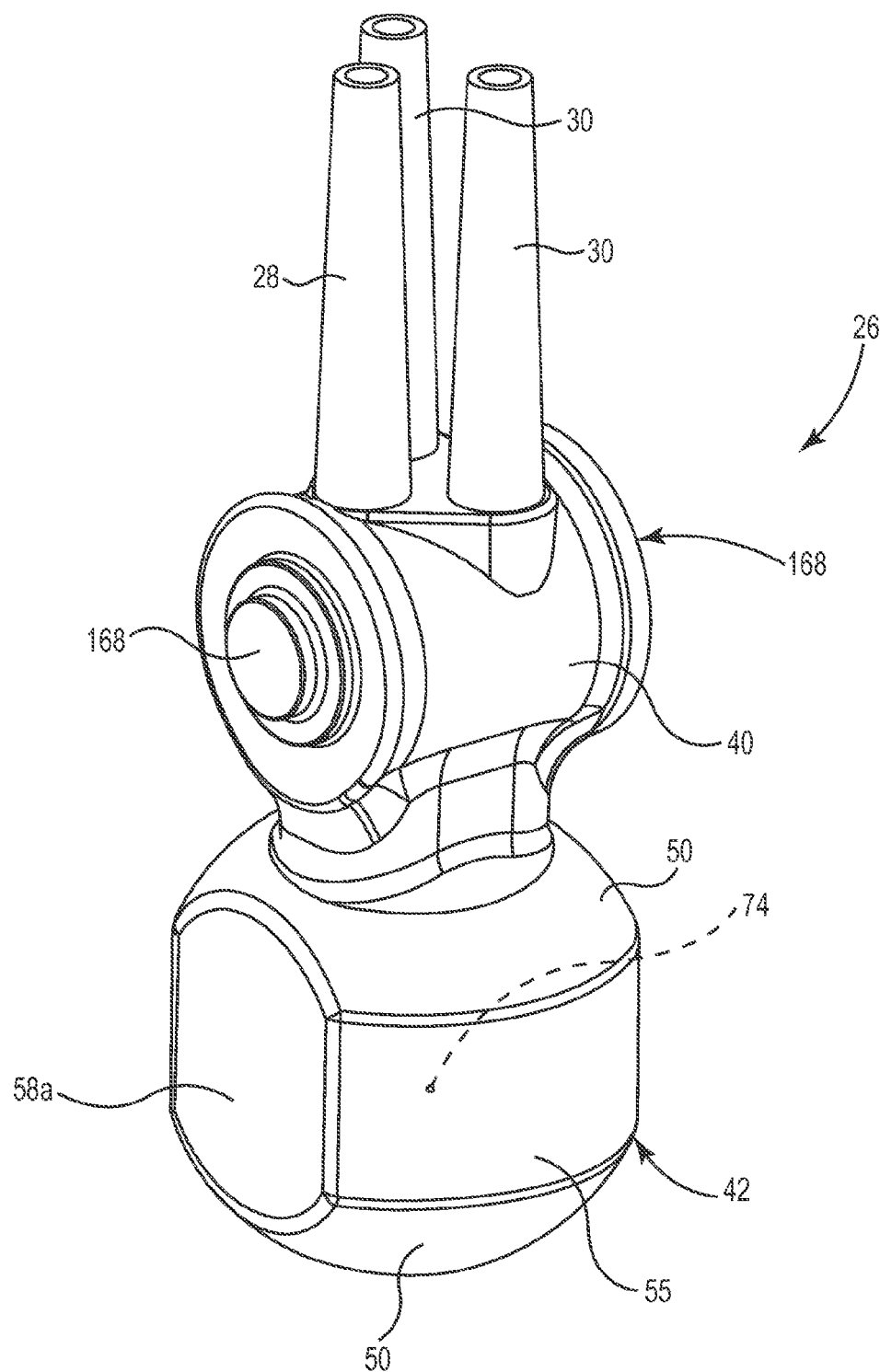
FIG. 10 is a perspective view of one embodiment of a pump suitable for use with the penile prosthetic illustrated in FIG. 1.

FIG. 10 is a perspective view of one embodiment of a pump 26 suitable for use with the penile prosthetic illustrated in FIG. 1. The pump 26 includes a pump housing 40 and a pump bulb 42. The housing 40 holds one or more valves that control the flow of liquid out of the pump bulb 42. In one embodiment, the pump bulb 42 is attached to the pump housing 40 such that the external surface of each of the segments 58a, 58b face towards a plane that is parallel with another plane including an activation surface 168 on the pump housing 40 (as shown in FIG. 10). In other embodiments, the pump bulb 42 is attached to the pump housing 40 such that the external surface of each of the segments 58a, 58b face towards a plane that is perpendicular to another plane including the activation surface 168 on the pump housing 40. In other words, the pump bulb 42 can be attached such that it is rotated 90 degrees in relation to the pump housing 40. Examples of this embodiment are shown in FIGS. 6 and 8. The specific configuration of the attachment of the pump bulb 42 to the pump housing 40 can be adjusted according to parameters such as, but not exclusively, patient anatomy and the preferred surgical procedure for the implantation.

The pump bulb 42 has an internal cavity 74 (schematically indicated with punctured line in FIG. 10) that is defined (surrounded) by six interconnected segments 50, 52, 55, 57, 58a, 58b (segments 57 and 58b not visible in FIG. 10). The six interconnected segments form an outer circumference of the pump bulb 42. The pump bulb 42 forms two finger pads located at the external surface of the side segments 58a, 58b. Each finger pad is spaced apart from the other finger pad by the segments 50, 52, 55 and 57.

Figure 11:
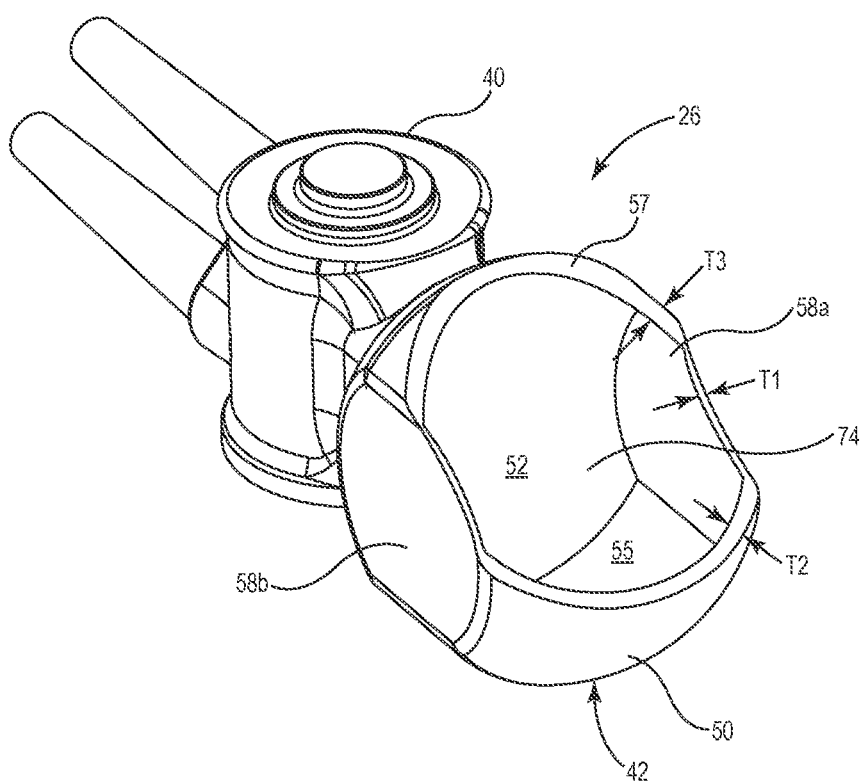
FIG. 11 is a schematic, perspective view of the pump bulb with a portion of the pump bulb cut away.

FIG. 11 is a schematic, perspective view of the pump bulb 42 with a portion of the pump bulb cut away for better illustration of the internal cavity 74. The pump bulb 42 is cut off such that a portion of each of the third and fourth side segments 58a, 58b; the top segment 50, and the second arc-shaped segment 57 is removed. The bottom segment 52 is attached to the pump housing 40. In one embodiment, six interconnected side segments define the internal cavity 74. In one embodiment, a thickness T2 of the top segment 50 is greater than a thickness T1 of the third side segment 58a. In one embodiment, a thickness T3 of the second arc-shaped segment 57 is greater than the thickness T1. In one embodiment, the thickness T2 corresponds to the thickness T3. In one embodiment, a thickness of the bottom segment 52 (thickness not indicated) corresponds to the thickness T2 of the top segment 50. In one embodiment, a thickness of the first arc-shaped segment 55 (thickness not indicated) corresponds to the thickness T3 of the second arc-shaped segment 57. Differentiating the thicknesses of the individual segments can help adjust and control the resistance to compression of the pump bulb 42 and thus facilitate controlling the tactile response to the user's thumb and finger, in turn helping to guide the user to engage and compress the correct external surfaces of the pump bulb 42.

Figure 12:
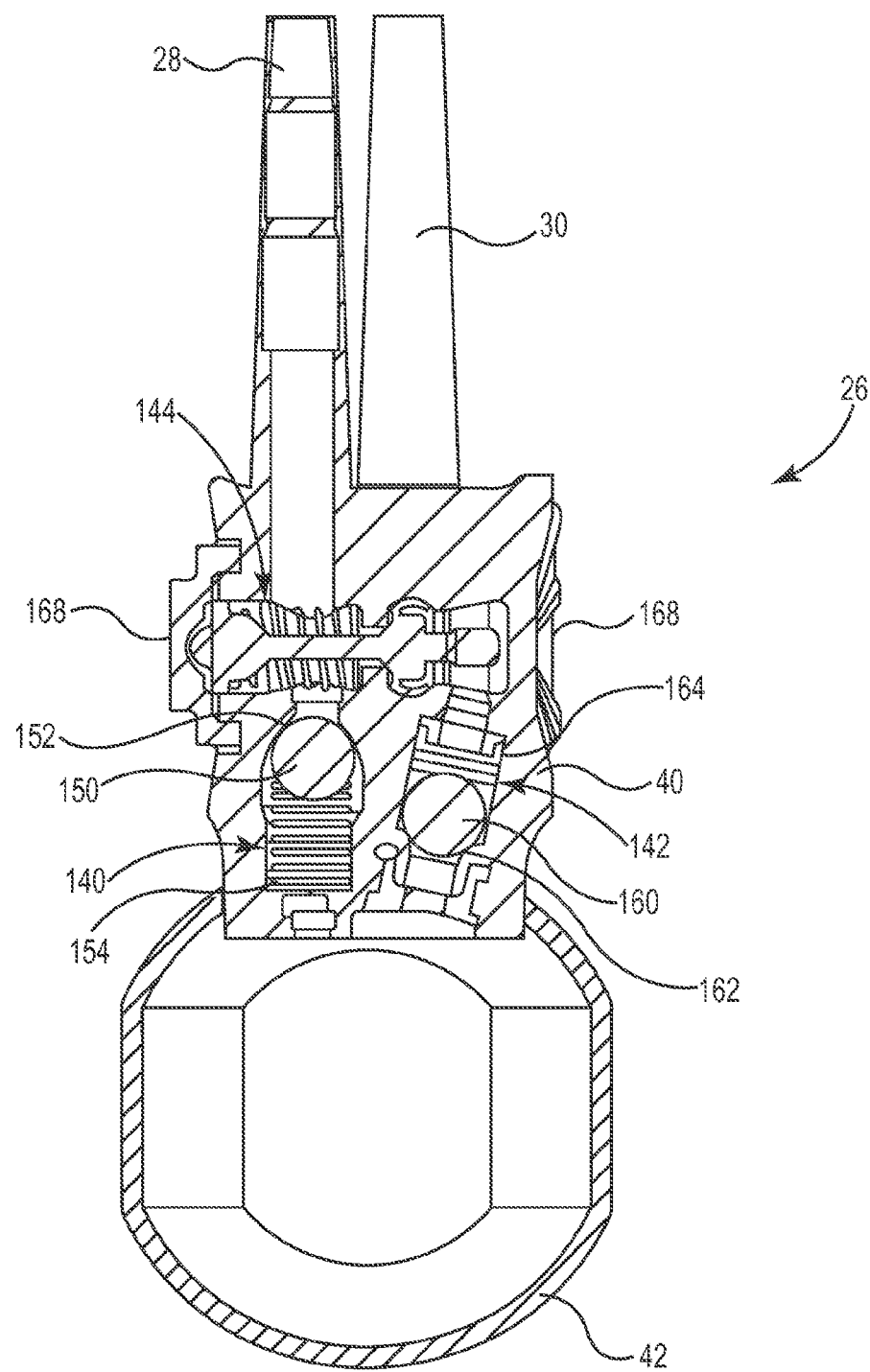
FIG. 12 is a longitudinal cross-sectional view of one embodiment of a pump suitable for use with the penile prosthesis system shown in FIG. 1.

FIG. 12 is a longitudinal cross-sectional view of one embodiment of a pump 26 suitable for use with the penile prosthesis system 20 shown in FIG. 1 having a pump bulb 42. FIG. 12 further includes illustration of the valve assemblies of the pump housing 40.

In one embodiment, the pump housing 40 includes an inlet valve 140 that communicates between the reservoir 22 (FIG. 1) and the pump bulb 42, an exhaust valve 142 that communicates between the pump bulb 42 and the cylinders 24, and a deflate valve 144 disposed in the pump housing 40 transversely between the inlet valve 140 and the exhaust valve 142.

The inlet valve 140 includes a ball 150 that is biased into contact with a surface 152 by a spring 154. The ball 150 is configured to be displaced from the surface 152 (thus compressing the spring 154) when liquid flows from the reservoir through the inlet tube 28 and into the pump bulb 42. When the liquid flow from the reservoir is reduced, or more specifically, when the pressure driving the liquid flow from the reservoir is reduced, the spring 154 biases the ball 150 into contact with the surface 152 to seat the ball 150 on the surface 152 and block backflow of the liquid from the bulb 102 back to the reservoir. In this manner, the inlet valve 140 provides a one-way inlet valve.

The exhaust valve 142 includes a ball 160 that is biased into contact with a surface 162 by a spring 164. The ball 160 is configured to be displaced from the surface 162 (thus compressing the spring 164) when liquid flows from the pump bulb 42 through the exhaust valve 142 toward the cylinders. For example, compressing the pump bulb 42 ejects liquid from the pump bulb 42, which unseats the ball 160 from the surface 162 to allow the liquid to flow past the ball 160 and the deflate valve 144 into the cylinders. Expansion (or recovery) of the pump bulb 42 draws liquid from the reservoir, past the ball 160, and into the bulb 102. The spring 164 biases the ball 160 into contact with the surface 162 to block backflow of liquid from the cylinders into the pump bulb 42. In this manner, the exhaust valve 142 provides a one-way exhaust valve.

The deflate valve 144 is configured to allow liquid to flow from the reservoir 22 into the pump bulb 42 and out the pump bulb 42 into the cylinders 24 during inflation of the cylinders (FIG. 1) as described above. The deflate valve 144 is also configured to allow for the rapid deflation of the cylinders 24. For example, in one embodiment pressing on the activation surface 168 moves the deflate valve 144 to the right in the orientation of FIG. 10, which allows fluid to flow from the cylinders 24 axially along the deflate valve 144 directly back into the reservoir 22.

Suitable materials for fabricating the pump 26 include silicone, polymers such as urethanes, a blend of polymers with urethane, copolymers of urethane, or the like. In one exemplary fabrication process, one of the suitable materials identified above is moulded into the shape of the pump bulb 42 illustrated in one of FIG. 1-6, 8 or 10.

Figure 13:
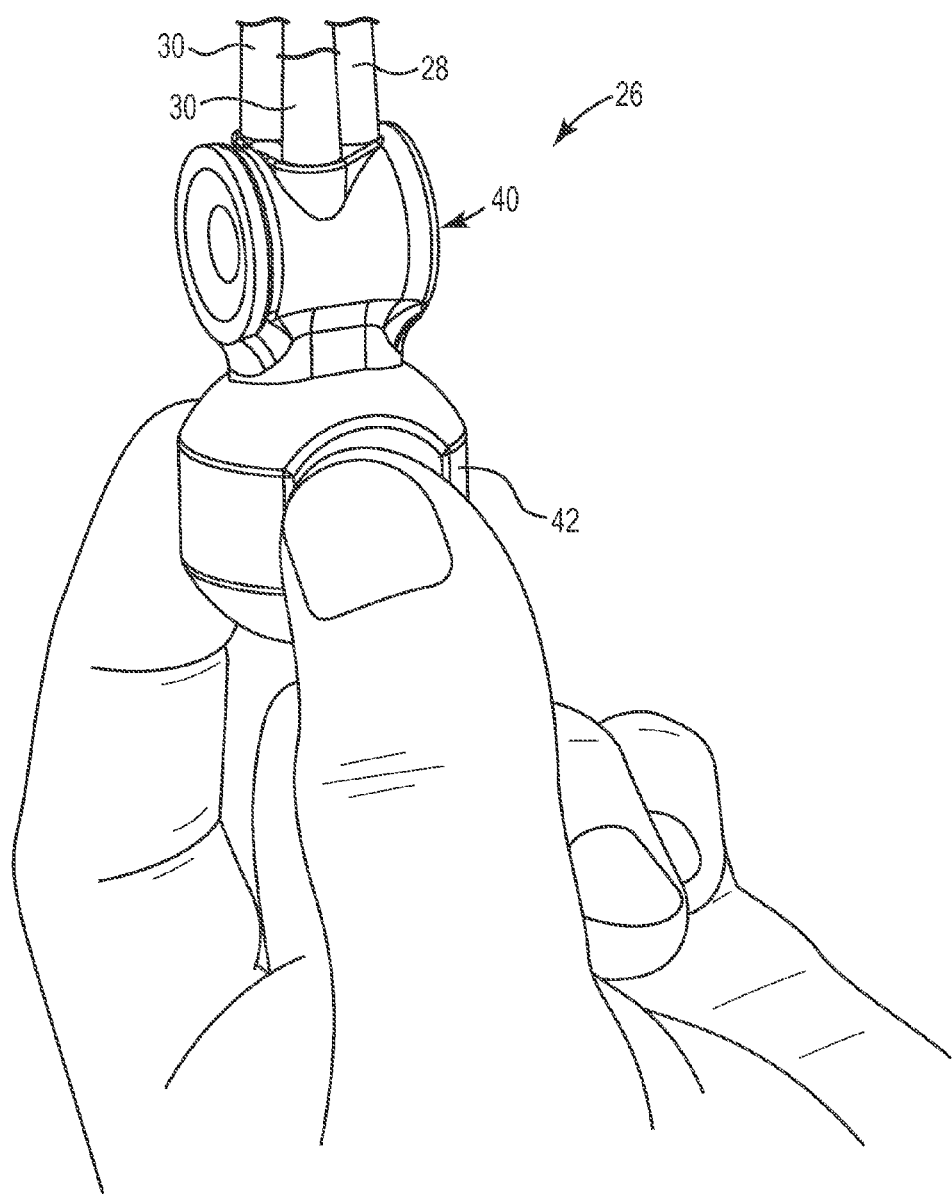
FIG. 13 is a perspective view of a hand accessing a finger gripping area on one embodiment of a pump bulb.

FIG. 13 is a schematic view of a hand grasping the pump 26. The pump 26 is sized to be implanted within the scrotum. However, the operation of the pump 26 and the improved grasping surfaces are best understood in isolation from the tissues of the body. The pump bulb 42 provides a concave portion 58a, 58b defined between first and second end sections 50, 52 and mid-section 54. The concave portion 58a is configured to receive the pad of the thumb, and another concave portion 58b (not shown) is sized to receive the pad of a finger, such as, but not limited to, an index finger. The first and second end section 50, 52 and the mid-section 54 direct the thumb and the finger to the appropriate concave portion 58, 58B and provide a structural exterior feature that is easy to locate.

In one embodiment, the exterior surface of the pump 26 is smooth and the user is allowed to grasp the pump bulb 42 by virtue of the concave portions 58a, 58b in conjunction with the mid-section 54. In one embodiment, the exterior surface of the pump bulb 42 is fabricated to have increased wet sliding friction provided by a plurality of ribs, a saw tooth pattern, bumps, or other external surface feature added to the exterior surface.

Figure 14:
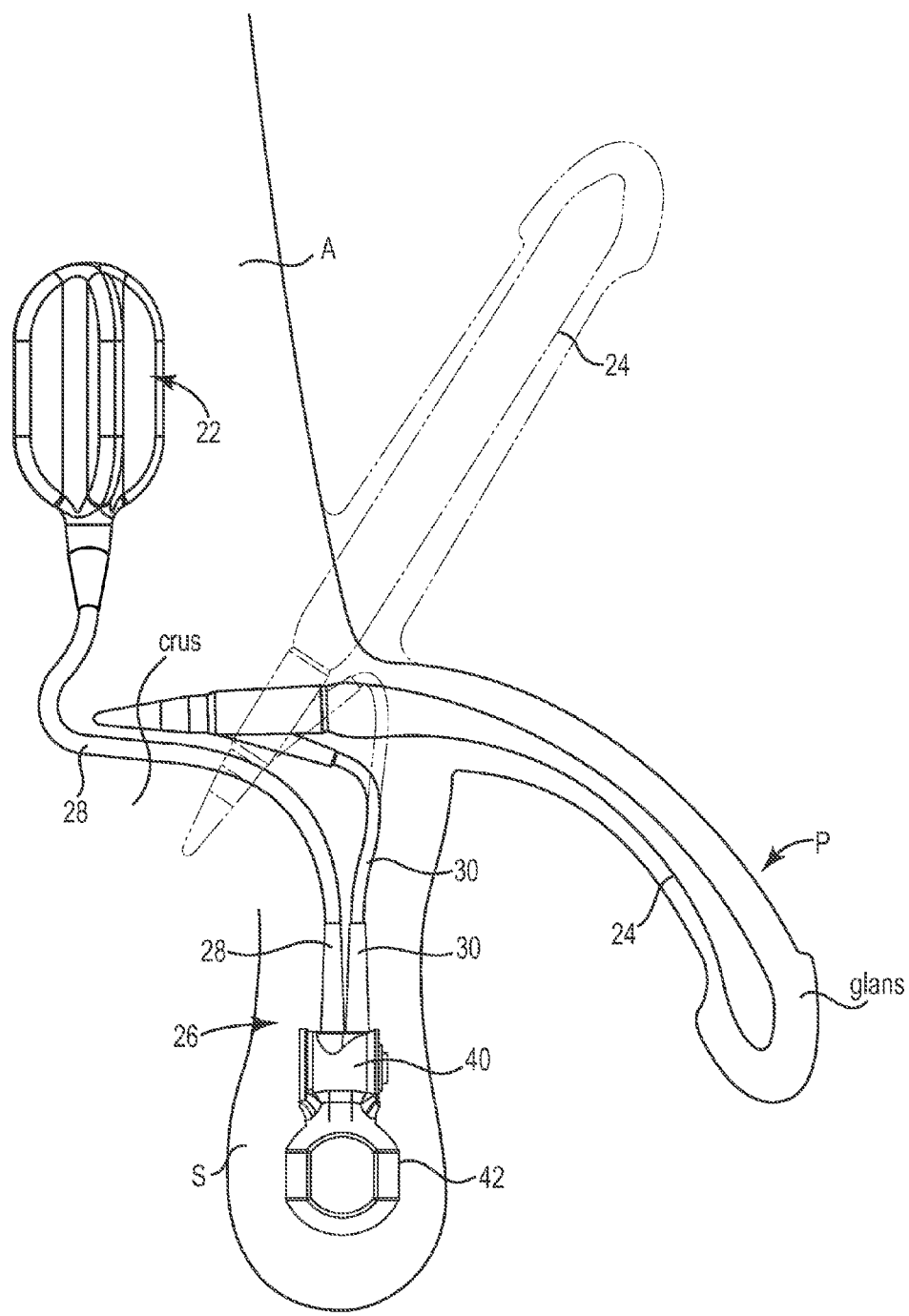
FIG. 14 is a schematic view of one embodiment of the implantable penile prosthetic system of FIG. 1 implanted in a user.

FIG. 14 is a schematic view of the reservoir 22 implanted in an abdomen A and the pair of cylinders 24 implanted in a penis P with the pump 26 intra-operatively connected to the reservoir 22 by the tubing 28 and connected to the cylinders 24 by the tubing 30.

The reservoir 22 is suitable for implantation into the abdomen behind the abdominal fascia, or in the space of Retzius, or another suitable location determined by the surgeon. The cylinders 24 are implanted into the penis from a proximal location at the crus to a distal location at the glans.

The pump 26 is implanted in the scrotum S in a manner that allows the user to manually access both pump housing 40 and the pump bulb 42. The concave portions 58a, 58b (FIGS. 5, 10) in cooperation with the first and second end sections 50, 52 and the mid-section 54 direct the user's finger and thumb to the external surface at the concave portions 58a, 58b and into a position that allows for maximum compression of the bulb 42. The concavity in combination with the mid- and end-sections provide a pump bulb 42 that is easier to manually locate and subsequently squeeze when inflating the cylinders 24 of the penile prosthetic.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An implantable penile prosthetic comprising:
an inflatable member that is sized for implantation into a penis of a user;
a reservoir that is implantable in an abdomen, the reservoir is configured to contain liquid useful in inflating the inflatable member; and
a pump that is intraoperatively attachable between the inflatable member and the reservoir, the pump configured to communicate with the inflatable member and the reservoir and sized for implantation into a scrotum, the pump including a pump bulb comprising:
a first end section and a second end section, each of the first end section and the second end section formed as a portion of a sphere;
a mid-section extending between the first end section and the second end section, with the mid-section planar in longitudinal cross-section and forming an arc in lateral cross-section; and a first concave portion being arced in longitudinal cross-section between a first apex located in the first end section and a second apex located in the second end section.

2. The penile prosthetic of claim 1, further comprising a second concave portion separate from the first concave portion, the second concave portion extending between a third apex located in the first end section and a fourth apex located in the second end section.

3. The penile prosthetic of claim 2, wherein the first concave portion and the second concave portion are located on opposite sides of the pump bulb, with the mid-section connected between the first concave portion and the second concave portion.

4. The penile prosthetic of claim 1, wherein a boundary of the mid-section is formed by a plurality of discrete segments.

5. The penile prosthetic of claim 4, wherein the mid-section comprises a first arc-shaped segment and a second arc-shaped segment, each of the first and the second arc-shaped segment extending between the first concave portion and the second concave portion.

6. The penile prosthetic of claim 1, wherein the mid-section forms a circular arc in lateral cross-section.

7. The penile prosthetic of claim 1, further comprising a second concave portion separate from the first concave portion, wherein the mid-section includes a band that is connected between the first concave portion and the second concave portion, and the band is narrower than a width of either of the first concave portion and the second concave portion.

8. The penile prosthetic of claim 1, wherein the concave portion is bounded by a first curved line located in the first end section and a second curved line located in the second end section, where the concave portion and the first and second curved lines form a finger gripping area of the pump bulb.

9. The penile prosthetic of claim 1, wherein the concave portion has a boundary provided by a first curved line located in the first end section, a second curved line located in the second end section, and a pair of separated and parallel linear lines connected between the first curved line located in the first end section and the second curved line located in the second end section.

10. The penile prosthetic of claim 1, wherein the second end section is attached to a pump housing.

11. The penile prosthetic of claim 1, further comprising a transition area between any two adjacent sections.

12. An implantable penile prosthetic comprising:
a inflatable member that is sized for implantation into a penis of a user;
a reservoir that is implantable in an abdomen, the reservoir is configured to contain liquid useful in inflating the inflatable member; and
a pump that is intraoperatively attachable between the inflatable member and the reservoir, the pump configured to communicate with the inflatable member and the reservoir and sized for implantation into a scrotum, the pump including:
a pump bulb having an internal cavity formed by an external surface, the external surface comprising six interconnected segments including:
a top segment formed as a portion of a top sphere surface, with a centre of the top sphere surface offset away from a centre of the internal cavity;
a bottom segment formed as a portion of a bottom sphere surface, with a centre of the bottom sphere surface offset away from the centre of the internal cavity;
a first arc-shaped side segment and a second arc-shaped side segment connecting the top segment with the bottom segment; and
a third side segment shaped as a portion of a sphere and a fourth side segment shaped as a portion of a sphere, each of the third and the fourth side segment connecting the top segment with the bottom segment such that the external surface at the third side segment and the fourth side segment defines a concavity.

13. The penile prosthetic of claim 12, wherein the first arc-shaped side segment is connected to the top segment along a first curved line and to the bottom segment along a second curved line, and wherein the second arc-shaped side segment is connected to the top segment along a third curved line and to the bottom segment along a fourth curved line.

14. The penile prosthetic of claim 13, wherein the first arc-shaped side segment is connected to the third side segment along a first straight line and to the fourth side segment along a second straight line, and wherein the second arc-shaped side segment is connected to the third side segment along a third straight line and to the fourth side segment along a fourth straight line.

15. The penile prosthetic of claim 13, wherein the third side segment is connected to the top segment along a fifth curved line and to the bottom segment along a sixth curved line, and wherein the fourth side segment is connected to the top segment along a seventh curved line and to the bottom segment along an eighth curved line.

16. The penile prosthetic of claim 12, wherein the pump bulb comprises a transition area between any two adjacent segments.

17. The penile prosthetic of claim 12, wherein a first width between an external surface of the first arc-shaped side segment and an external surface of the second arc-shaped side segment is greater than a second width between an external surface of the third side segment and an external surface of the fourth side segment.

18. The penile prosthetic of claim 1, wherein a profile of the first concave portion is arced between portions of the mid-section in lateral cross-section.

19. The penile prosthetic of claim 1, wherein the first concave portion is spherically shaped.

* * * * *